(12) United States Patent
Chen et al.

(10) Patent No.: US 7,952,711 B1
(45) Date of Patent: May 31, 2011

(54) WAVEPLATE ANALYZER BASED ON MULTIPLE TUNABLE OPTICAL POLARIZATION ROTATORS

(75) Inventors: Xiaojun Chen, San Gabriel, CA (US); Lianshan Yan, Sichuan (CN); Xiaotian Steve Yao, Diamond Bar, CA (US)

(73) Assignee: General Photonics Corporation, Chino, CA (US)

( * ) Notice: Subject to any disclaimer, the term of this patent is extended or adjusted under 35 U.S.C. 154(b) by 367 days.

(21) Appl. No.: 12/056,262

(22) Filed: Mar. 26, 2008

Related U.S. Application Data

(60) Provisional application No. 60/908,124, filed on Mar. 26, 2007.

(51) Int. Cl.
*G01J 4/00* (2006.01)
(52) U.S. Cl. .......................... 356/365; 356/364; 356/367
(58) Field of Classification Search .......... 356/364–370; 359/259, 279, 280
See application file for complete search history.

(56) References Cited

U.S. PATENT DOCUMENTS

| | | | |
|---|---|---|---|
| 3,302,028 A | 1/1967 | Sterzer | |
| 3,684,350 A | 8/1972 | Wentz | |
| 3,719,414 A | 3/1973 | Wentz | |
| 4,389,090 A | 6/1983 | LeFevre | |
| 4,461,543 A | 7/1984 | McMahon | |
| 4,798,436 A | 1/1989 | Mortimore | |
| 5,004,312 A | 4/1991 | Shimizu | |
| 5,111,322 A | 5/1992 | Bergano et al. | |
| 5,153,676 A | 10/1992 | Bergh | |
| 5,251,057 A | 10/1993 | Guerin et al. | |
| 5,317,445 A | 5/1994 | DeJule et al. | |
| 5,373,393 A | 12/1994 | DeJule et al. | |
| 5,381,250 A | 1/1995 | Meadows | |
| 5,473,457 A | 12/1995 | Ono | |
| 5,475,525 A | 12/1995 | Tournois et al. | |
| 5,561,726 A | 10/1996 | Yao | |
| 5,611,005 A | 3/1997 | Heismann et al. | |
| 5,627,645 A * | 5/1997 | Imagawa et al. | 356/364 |
| 5,723,856 A | 3/1998 | Yao et al. | |
| 5,751,747 A | 5/1998 | Lutes et al. | |
| 5,777,778 A | 7/1998 | Yao | |
| 5,796,510 A | 8/1998 | Yao | |
| 5,835,270 A | 11/1998 | Urino et al. | |
| 5,917,179 A | 6/1999 | Yao | |
| 5,929,430 A | 7/1999 | Yao et al. | |
| 5,930,414 A | 7/1999 | Fishman et al. | |
| 5,978,125 A | 11/1999 | Yao | |
| 6,178,036 B1 | 1/2001 | Yao | |
| 6,181,728 B1 | 1/2001 | Cordingley et al. | |
| 6,229,937 B1 | 5/2001 | Nolan et al. | |
| 6,252,711 B1 | 6/2001 | Damask et al. | |

(Continued)

OTHER PUBLICATIONS

Damask, J.N., "A Programmable Polarization-Mode Dispersion Emulator for Systematic Testing of 10 Gb/s PMD Compensators," *Optical Fiber Communication Conference*, vol. 3, pp. 28-30, Mar. 2000.

(Continued)

*Primary Examiner* — Sang Nguyen
(74) *Attorney, Agent, or Firm* — Perkins Coie LLP

(57) ABSTRACT

Systems, apparatus and methods for characterizing linear retarders using a waveplate analyzer constructed by polarization rotators. In one implementation of such an analyzer, both the retardation of the waveplate sample and the orientation of optical axis of the waveplate sample can be simultaneously measured.

14 Claims, 4 Drawing Sheets

U.S. PATENT DOCUMENTS

| | | |
|---|---|---|
| 6,339,489 B1 | 1/2002 | Bruyere et al. |
| 6,377,719 B1 | 4/2002 | Damask |
| 6,388,785 B2 | 5/2002 | Havstad et al. |
| 6,389,197 B1 | 5/2002 | Ilchenko et al. |
| 6,417,948 B1 | 7/2002 | Chowdhury et al. |
| 6,417,957 B1 | 7/2002 | Yao |
| 6,473,218 B1 | 10/2002 | Maleki et al. |
| 6,476,959 B2 | 11/2002 | Yao |
| 6,480,637 B1 | 11/2002 | Yao |
| 6,487,233 B2 | 11/2002 | Maleki et al. |
| 6,487,336 B1 | 11/2002 | Yao |
| 6,488,861 B2 | 12/2002 | Iltchenko et al. |
| 6,493,116 B1 | 12/2002 | Robinson et al. |
| 6,493,474 B1 | 12/2002 | Yao |
| 6,498,869 B1 | 12/2002 | Yao |
| 6,535,328 B2 | 3/2003 | Yao |
| 6,542,650 B2 | 4/2003 | Khosravani et al. |
| 6,546,159 B1 | 4/2003 | Peng et al. |
| 6,552,833 B2 | 4/2003 | Liu et al. |
| 6,567,167 B1 | 5/2003 | Chou et al. |
| 6,567,436 B1 | 5/2003 | Yao et al. |
| 6,576,886 B1 | 6/2003 | Yao |
| 6,577,445 B1 | 6/2003 | Damask |
| 6,580,532 B1 | 6/2003 | Yao et al. |
| 6,594,061 B2 | 7/2003 | Huang et al. |
| 6,604,871 B2 | 8/2003 | Cao |
| 6,628,850 B1 | 9/2003 | Yao |
| 6,628,861 B1 | 9/2003 | Yao |
| 6,628,862 B1 | 9/2003 | Yao |
| 6,643,064 B2 | 11/2003 | Huang et al. |
| 6,661,941 B1 | 12/2003 | Yao |
| 6,671,464 B1 | 12/2003 | Kikuchi |
| 6,687,423 B1 | 2/2004 | Yao |
| 6,707,977 B2 | 3/2004 | Chien et al. |
| 6,731,389 B2 | 5/2004 | Luscombe et al. |
| 6,754,404 B2 | 6/2004 | Yao |
| 6,795,481 B2 | 9/2004 | Maleki et al. |
| 6,795,616 B2 | 9/2004 | Yao |
| 6,836,327 B1 | 12/2004 | Yao |
| 6,842,283 B2 | 1/2005 | Savory et al. |
| 6,847,484 B2 | 1/2005 | Damask et al. |
| 6,856,400 B1 | 2/2005 | Froggatt |
| 6,867,918 B2 | 3/2005 | Damask |
| 6,873,631 B2 | 3/2005 | Yao et al. |
| 6,873,783 B1 | 3/2005 | Yao |
| RE38,735 E | 5/2005 | Yao |
| 6,891,616 B2 | 5/2005 | Saitoh et al. |
| 6,891,674 B2 | 5/2005 | Damask |
| 6,900,932 B2 | 5/2005 | Chen et al. |
| 6,937,798 B1 | 8/2005 | Yao et al. |
| RE38,809 E | 10/2005 | Yao |
| 6,975,454 B1 | 12/2005 | Yan et al. |
| 7,027,135 B2 | 4/2006 | Fu et al. |
| 7,027,198 B2 | 4/2006 | Yao |
| 7,067,795 B1 | 6/2006 | Yan et al. |
| 7,068,896 B1 | 6/2006 | Kath et al. |
| 7,076,169 B2 | 7/2006 | Shpantzer et al. |
| 7,079,247 B2 * | 7/2006 | Shribak et al. ............ 356/364 |
| 7,154,659 B1 | 12/2006 | Yao et al. |
| 7,157,687 B1 | 1/2007 | Yao |
| 7,218,436 B2 | 5/2007 | Yao |
| 7,227,686 B1 | 6/2007 | Yan et al. |
| 7,233,720 B2 | 6/2007 | Yao |
| 7,245,952 B2 * | 7/2007 | Cameron ................... 600/319 |
| 7,265,836 B1 | 9/2007 | Yao |
| 7,265,837 B1 | 9/2007 | Yao |
| 7,301,632 B2 * | 11/2007 | Hug ........................... 356/364 |
| 7,343,100 B2 | 3/2008 | Yao |
| 7,372,568 B1 | 5/2008 | Yao |
| 7,382,962 B1 | 6/2008 | Yao |
| 7,391,977 B2 | 6/2008 | Yao |
| 7,436,569 B2 | 10/2008 | Yao et al. |
| 7,466,471 B2 | 12/2008 | Yao |
| 7,522,785 B2 | 4/2009 | Yao |
| 7,534,990 B2 | 5/2009 | Yao |
| 7,535,639 B2 | 5/2009 | Yao et al. |
| 7,693,419 B1 | 4/2010 | Chen et al. |
| 7,796,894 B1 | 9/2010 | Yao |
| 2001/0052981 A1 | 12/2001 | Chung et al. |
| 2002/0015547 A1 | 2/2002 | Patel |
| 2002/0075477 A1 | 6/2002 | Yu et al. |
| 2002/0191265 A1 | 12/2002 | LaGasse et al. |
| 2003/0007151 A1 | 1/2003 | Eckert |
| 2003/0035120 A1 | 2/2003 | Myatt et al. |
| 2003/0076588 A1 | 4/2003 | Savory et al. |
| 2003/0081874 A1 | 5/2003 | Yao |
| 2003/0156776 A1 | 8/2003 | Han et al. |
| 2003/0206689 A1 | 11/2003 | Jung et al. |
| 2004/0037495 A1 | 2/2004 | Yao |
| 2004/0247226 A1 | 12/2004 | Pyo et al. |
| 2005/0041922 A1 | 2/2005 | Yao |
| 2005/0129346 A1 | 6/2005 | Chen et al. |
| 2005/0168659 A1 | 8/2005 | Melton |
| 2005/0200941 A1 | 9/2005 | Yao |
| 2005/0201751 A1 | 9/2005 | Yao |
| 2005/0265728 A1 | 12/2005 | Yao |
| 2006/0023987 A1 | 2/2006 | Yao |
| 2006/0115199 A1 | 6/2006 | Yao |
| 2006/0245706 A1 | 11/2006 | Kath et al. |
| 2007/0223078 A1 | 9/2007 | Yao et al. |
| 2007/0297054 A1 | 12/2007 | Yao et al. |
| 2008/0030839 A1 | 2/2008 | Yao |
| 2008/0054160 A1 | 3/2008 | Yao |
| 2008/0138070 A1 | 6/2008 | Yan et al. |
| 2008/0159692 A1 | 7/2008 | Yao |
| 2009/0028565 A1 | 1/2009 | Yao |
| 2009/0207409 A1 | 8/2009 | Yao |
| 2009/0213453 A1 | 8/2009 | Yao |
| 2009/0225420 A1 | 9/2009 | Yao et al. |
| 2009/0238218 A1 | 9/2009 | Yao |
| 2010/0239245 A1 | 9/2010 | Yao |

OTHER PUBLICATIONS

Damask, J.N., et al., "Demonstration of a Coherent PMD Source," *IEEE Photonics Technology Letters*, 15(11):1612-1614, Nov. 2003.

Foschini, G.J., et al., "Probability Densities of Second-Order Polarization Mode Dispersion Including Polarization Dependent Chromatic Fiber Dispersion," *IEEE Photonics Technology Letters*, 12(3):293-295, Mar. 2000.

Hauer, M.C., et al., "Electrically Controllable All-Fiber PMD Emulator Using a Compact Array of Thin-Film Microheaters," *Journal of Lightwave Technology*, 22(4):1059-1065, Apr. 2004.

Karlsson, M., et al., "Autocorrelation function of the polarization-mode dispersion vector," *Optics Letters*, 24(14):939-941, Jul. 1999.

Kogelnik, H., et al., *Optical Fiber Telecommunications IV B Systems and Impairments*, Chapter 15 "Polarization-Mode Dispersion", pp. 725-861, I.P. Kaminow and T. Li, Eds. Academic Press, 2002.

Lee, J.H., et al., "Statistical PMD Emulator Using Variable DGD Elements," *Optical Communication Conference and Exhibit*, OFC 2002, pp. 375-376, Mar. 2002.

Lima, I.T., et al., "Comparison of Polarization Mode Dispersion Emulators," *Journal of Lightwave Technology*, 19(12):1872-1881, Dec. 2001.

Noé, R., et al., "Polarization Mode Dispersion Compensation at 10, 20, and 40 Gb/s with Various Optical Equalizers," *Journal of Lightwave Technology*, 17(9):1602-1616, Sep. 1999.

Willner, A.E., et al., "PMD Emulation," *Journal of Optical and Fiber Communications Research*, 1(3):181-200, Nov. 2004.

Yan, L.-S., et al., "Polarization-Mode-Dispersion Emulator Using Variable Differential-Group-Delay (DGD) Elements and Its Use for Experimental Importance Sampling," *Journal of Lightwave Technolology*, 22(4):1051-1058, Apr. 2004.

Lima, A.O., et al., "Statistical Analysis of the Performance of PMD Compensators Using Multiple Importance Sampling," IEEE Photonics Technology Letters, 15(2):1716-1718, Dec. 2003.

Azzam, R.M.A., "Photopolarimeter using two modulated optical rotators", *Optics Letters*, 1(5):181-183, Nov. 1977.

Chipman, R.A., *Handbook of Optics*, vol. II, Chapter 22—Polarimetry, 2nd Ed. M. Bass ed., McGraw-Hill, New York, 1995.

Collett, E., *Polarized Light in Fiber Optics*, Chapters 15-16, The PolaWave Group, New Jersey, 2003.

Compain, E., et al., "General and Self-Consistent Method for the Calibration of Polarization Modulators, Polarimeters, and Mueller-Matrix Ellipsometers", *Applied Optics*, 38(16):3490-3502, Jun. 1999.

De Martino, A., et al., "Optimized Mueller polarimeter with liquid crystals", *Optics Letters*, 28(8):616-618, Apr. 2003.

Goldstein, D.H., et al., "Error analysis of a Mueller matrix polarimeter", *J. Opt. Soc. Am. A*, 7(4):693-700, Apr. 1990.

Goldstein, D.H., *Polarized Light*, Chapter 29, 2nd Ed., Marcel Dekker, New York, 2003.

Khosravani, R., et al., "Time and Frequency Domain Characteristics of Polarization-Mode Dispersion Emulators," *IEEE Photonics Technology Letters*, 13(2):127-129, Feb. 2001.

Rochford, K.B., et al., "Accurate Interferometric Retardance Measurements," *Applied Optics*, 36(25):6473-6479, Sep. 1997.

Sobiski, D., et al., "Fast first-order PMD compensation with low insertion loss for 10Gbit/s system," *Electronics Letters*, 37(1):46-48, Jan. 2001.

Wang, S.X., et al., "Fast wavelength-parallel polarimeter for broadband optical networks", *Optics Letters*, 29(9):923-925, May 2004.

Williams, P., "Rotating-Polarizer Polarimeter for Accurate Retardance Measurement," *Applied Optics*, 36(25):6466-6472, Sep. 1997.

Williams, P., "Rotating-Wave-Plate Stokes Polarimeter for Differential Group Delay Measurements of Polarization-Mode Dispersion", *Applied Optics*, 38(31):6508-6515, Nov. 1999.

Yan, L.-S., et al., "Experimental Importance Sampling Using a 3-Section PMD Emulator with Programmable DGD Elements," *Optical Fiber Communications Conference (OFC 2003)*, paper ThA4, 4 pages, Mar. 2003.

Yan, L.-S., et al., "High-Speed and Highly Repeatable Polarization-State Analyzer for 40-Gb/s System Performance Monitoring," *IEEE Photonics Technology Letters*, 18(4):643-645, Feb. 2006.

Yan, L.-S., et al., "High-Speed, Stable and Repeatable PMD Emulator with Tunable Statistics," *Optical Fiber Communication Conference (OFC 2003)*, paper MF6, 5 pages, Mar. 2003.

Yao, X. S., et al., "Highly repeatable all-solid-state polarization-state generator", *Optics Letters*, 30(11):1324-1326, Jun. 2005.

\* cited by examiner

US 7,952,711 B1

WAVEPLATE ANALYZER BASED ON MULTIPLE TUNABLE OPTICAL POLARIZATION ROTATORS

PRIORITY CLAIM AND RELATED PATENT APPLICATION

This application claims the benefit of U.S. Provisional Application No. 60/908,124 entitled "Waveplate Analyzer Based On Multiple Tunable Optical Polarization Rotators" and filed on Mar. 26, 2007, the disclosure of which is incorporated by reference as part of the specification of this application.

BACKGROUND

This application relates to systems, apparatus and methods related to optical polarization.

An optical waveplate can be used to generate linear retardation between two different polarization components of an optical signal and is an important device in various polarization-related analysis and control applications. Various methods can be used to measure the induced retardation of a waveplate, including methods using optical compensators, rotating retarders, rotating polarizers, rotating the sample in polarimeters and other polarization devices or systems. Some implementations of these and other polarization measurement methods suffer from slow speed, short lifetime, and high cost. Examples of other more complex methods for measuring the induced retardation of a waveplate include techniques utilizing electro-optic modulation, elastic-optic modulation, and interferometric configurations. These techniques can be effective measurement tools but some implementations cannot determine the retardation and optical axis simultaneously and thus have limited use in various applications.

SUMMARY

This application describes implementations and examples of systems, apparatus and methods for characterizing linear retarders using a waveplate analyzer constructed by polarization rotators. Such an analyzer can be configured and operated to simultaneously measure both the retardation of the waveplate sample and the orientation of optical axis of a waveplate sample.

In one aspect, an apparatus for measuring retardation induced by an optical element that exhibits birefringence can include polarization rotators to rotate the polarization of input polarized light, an output polarizer located downstream from the polarization rotators to receive light from the polarization rotators and a photodetector to receive light from the output polarizer and to measure the intensity of the light passing through the output polarizer. The polarization rotators include least a pair of polarization rotators located in front of a sample holder for holding a sample under test, and at least a pair of polarization rotators downstream from the sample holder. Each polarization rotator is adjustable in response to a control signal. The input of the apparatus may include a light source to produce light and a polarized light generator to operate on the light to generate desired polarized light that is directed into the polarization rotators, where the polarized light generator may include a combination of a linear polarizer and a waveplate (e.g., a quarter wave plate).

In another aspect, a method for measuring optical birefringence of a sample is described to include: directing an optical probe beam of an input state of polarization to sequentially pass through (1) at least two adjustable input polarization rotators, (2) a sample under measurement, (3) at least two adjustable output polarization rotators and (4) an output optical polarizer; adjusting the at least two adjustable input polarization rotators and at least two adjustable output polarization rotators to produce a plurality of different states of polarization in the optical probe beam when entering the output optical polarizer; measuring optical power levels of optical transmission of the optical probe beam through the output optical polarizer at the plurality of different states of polarization of the optical probe beam when entering the output optical polarizer; and performing a numerical processing based on the input state of polarization of the optical probe beam and the measured optical power levels at the plurality of different states of polarization on the optical probe beam when entering the output optical polarizer to determine an amount of the optical retardation of the sample and an orientation of a principal polarization axis of the sample.

In yet another aspect, a device for measuring optical birefringence of a sample is described to include an input optical polarization element operable to receive an optical probe beam and to output the optical probe beam at an input state of polarization; at least two adjustable input polarization rotators positioned to receive the optical probe beam from the input optical polarization element and each operable to rotate polarization of light; a sample holder operable to hold a sample and positioned to placed the sample in an optical path of the optical probe beam from the at least two adjustable input polarization rotators; at least two adjustable output polarization rotators positioned to receive the optical probe beam that passes through the sample holder and each operable to rotate polarization of light; an output optical polarizer positioned to receive the optical probe beam from the at least two adjustable output polarization rotators to produce an output optical probe beam polarized in a direction along a polarization direction of the output optical polarizer; and a photodetector positioned to receive the output optical probe beam from the output optical polarizer and operable to measure a power level of the output optical probe beam. This device also includes a control and processing unit operable to control the adjustable input and output polarization rotators to be at different collections of rotator settings to generate different states of polarization in the optical probe beam after transmitting through the at least two adjustable output polarization rotators to obtain different power levels of the output optical probe beam at the photodetector, respectively. The control and processing unit is programmed to perform a numerical processing based on the input state of polarization of the optical probe beam when exiting the input optical polarization element and the measured optical power levels at the plurality of different states of polarization of the optical probe beam when entering the output optical polarizer to determine an amount of the optical retardation of the sample and an orientation of a principal polarization axis of the sample.

These and other aspects of the systems, apparatus and methods for characterizing birefringence of optical materials and linear retarders are described in greater detail in the attached drawings, the detailed description and the claims.

DETAILED DESCRIPTION

This application describes, among others, systems, apparatus and methods based on an optical waveplate analyzer (WPA) using polarization rotators. Implementations of the described systems, apparatus and methods include use compact waveplate analyzers using binary magneto-optic (MO) rotators that have no moving parts, are compact, can operate at high speeds, and exhibit superior repeatability and stability. Example of WPAs described in this application can accurately and simultaneously measure the retardation of the waveplate and the orientation of optical axes. Specific examples of optical devices using a series of polarization rotators are described in U.S. Pat. No. 7,218,436 entitled "Optical Instrument and Measurements Using Multiple Tunable Optical Polarization Rotators" and can be used to implement the WPA analyzers described in this application. The entire disclosure of the U.S. Pat. No. 7,218,436 is incorporated by reference as part of the specification of this application.

One example of an present apparatus for measuring retardation induced by an optical element that exhibits birefringence can include polarization rotators to rotate the polarization of input polarized light, an output polarizer located downstream from the polarization rotators to receive light from the polarization rotators and a photodetector to receive light from the output polarizer and to measure the intensity of the light passing through the output polarizer. The polarization rotators include least a pair of polarization rotators located in front of a sample holder for holding a sample under test, and at least a pair of polarization rotators downstream from the sample holder. Each polarization rotator is adjustable in response to a control signal. The input of the apparatus may include a light source to produce light and a polarized light generator to operate on the light to generate desired polarized light that is directed into the polarization rotators, where the polarized light generator may include a combination of a linear polarizer and a waveplate (e.g., a quarter wave plate).

In operation, the state of polarization of the light generated by polarized light generator can be calibrated by measuring the signals received at the photodetector under different rotation states of the polarization rotators in absence of the sample. The retardance and orientation of the sample under test can be obtained by measuring the signals received at the photodetector under different rotation states of polarization rotators when the sample is placed in the sample holder through which the light passes through. The wavelength dependence of retardance of the sample under test can be measured by using the light source which wavelength can be tuned. The order of the waveplate sample under test can be determined according to the chromatic dispersion and the wavelength dependence of retardance of the sample.

Figure 1:
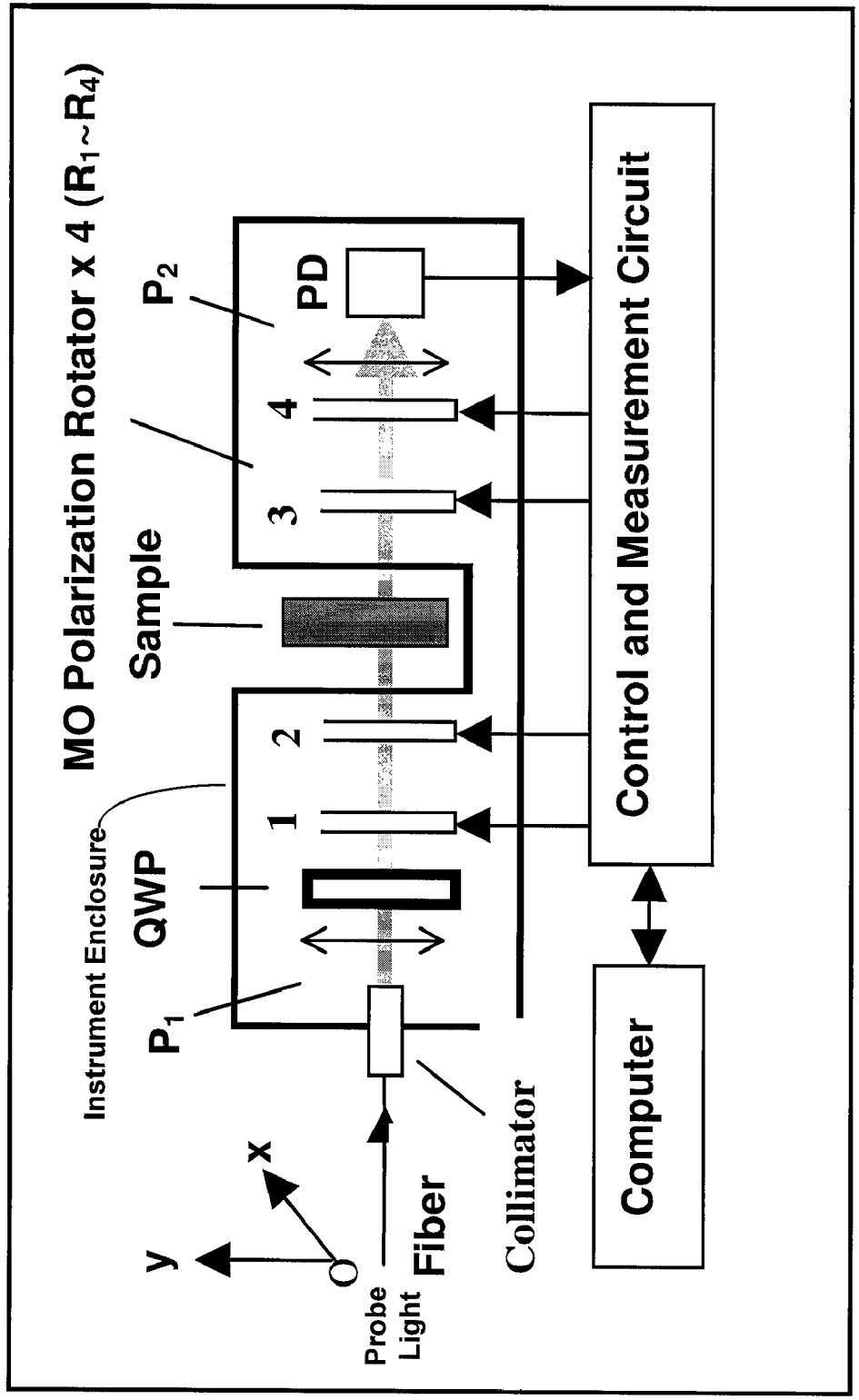
FIG. 1 shows an example of a waveplate analyzer (WPA) using four magneto-optic (MO) polarization rotators R1-R4, a polarizer (P1) tilted 22.5o from the vertical axis (y-axis), a polarizer (P2) and the fast-axis of $\lambda/4$ waveplate (QWP) both aligned vertically, where the rotation angles of polarization rotators are about ±22.5° at their central wavelength.

FIG. 1 shows one example of a waveplate analyzer (WPA) based on magneto-optic polarization rotators (MO-rotators) based on the above described design. In this example, a collimator is used to expand the input light (1500 nm to 1580 nm) to a parallel beam with a diameter of about 0.1 mm. The polarizer ($P_1$) is placed at the input of the system and is aligned with 22.5° from the fast axis of the λ/4 waveplate (QWP) to generate a right-hand elliptically polarized light.

The waveplate under test (sample) is inserted in the middle slot. Two pairs of MO rotators (1, 2, 3 and 4) are placed in front of and behind the sample to rotate the polarization plane, respectively. After passing through the sample, rotators and another polarizer ($P_2$), light enters the photodetector (PD), which is used to detect the light intensity changes under different rotation states of MO rotators. A low-noise transimpedance amplifier and 16-bit A/D converter converted the current of the photodetector to digital signals for computer data collection. A control and measurement circuit is provided to control the MO rotators 1, 2, 3 and 4 and to receive the detector output from the detector PD. A digital signal processing unit, e.g., a computer, is connected with the control and measurement circuit to perform the data processing based on the rotation angles of the MO rotators and the corresponding detector outputs and to control the rotations of the MO rotators. An instrument enclosure or housing is designed to enclose the optical components of the WPA device and to allow placement of the sample in and out of the optical path of the probe light. An input port is provided to include a collimator that is coupled to a fiber that guides the probe light from a light source such as a diode laser.

The MO rotators in this device have deterministic rotation property that can rotate the input state of polarization (SOP) by a precise angle around 22.5° or −22.5° when a positive or negative saturated magnetic field applies. Therefore, when two rotators rotate in the same direction, the net rotation is +45° or −45°. On the other hand, if two rotators rotate in the opposite direction, the net polarization rotation is zero. FIG. 1 shows that, for a given input SOP, the power detected by photodetector will change when the rotation status of MO rotators are changed. On the other hand, for different retardance and axis orientation of sample, the changes in detected power are different for the same rotation status of MO rotators. In fact, as will be shown below, the retardance and axis orientation of the sample can be calculated from the power measurements under different combinations of MO polarization rotations.

During testing, the rotators are set to different logic states, and the light intensity detected by the photodetector can be written as $$I_{out} = \frac{I_0}{2}\{1 + [-(\cos2(\alpha - \theta_{wp})\cos2(\beta + \theta_{wp}) + \sin2(\alpha - \theta_{wp})\sin2(\beta + \theta_{wp})\cos(\Gamma)]S_1 + [\sin2(\alpha - \theta_{wp})\cos2(\beta + \theta_{wp}) + \cos2(\alpha - \theta_{wp})\sin2(\beta + \theta_{wp})\cos(\Gamma)]S_2 + \sin2(\beta + \theta_{wp})\sin\Gamma S_3\} \quad (1)$$

where $I_0$ is the light intensity incident upon the sample, ($S_1$ $S_2$ $S_3$) are the normalized Stokes parameters of the light after passing through $P_1$ and QWP, $\theta_{wp}$ is the orientation angle of the fast axis of the waveplate sample with respect to the horizontal, and $\Gamma$ is the retardance of the sample. The angles $\alpha$ and $\beta$ are the total polarization rotation angles of the first pair of rotators (in front of the sample) and the second pair of rotators (after the sample), respectively, and they can be written as $$\alpha = \sum_{n=1}^{2} -(-1)^{bn}\theta \quad (2)$$

$$\beta = \sum_{n=3}^{4} -(-1)^{bn}\theta.$$

where $b_n$ (=0 or 1) is the binary value of the $n^{th}$ rotator (i.e. 0- or 1-state corresponds to negative or positive saturation field applied, respectively), $\theta=22.5+\Delta\theta$ is the rotation angle of the MO rotator when a magnetic field above saturation field is applied, and $\Delta\theta$ characterizes the change of rotation angle when temperature and operating wavelength deviate from the specifications of MO rotators.

Because of the binary nature of each MO rotator, $I_{out}$ has 16 possible values. One can easily find by inspecting FIG. 1 or Eq. (2) that $\alpha$ and $\beta$ only have three possible value $(0,2\theta,-2\theta)$, respectively. Therefore, $I_{out}$ in Eq. (1) only has $3\times3=9$ different values for all 16 states of rotators, as shown in Table 1. The rests are degenerate.

TABLE 1

Relationship of $\alpha$, $\beta$ and logic states of WPA

| $I_i$ | $\alpha$ | $\beta$ | Logic States $(R_1R_2R_3R_4)$ |
|---|---|---|---|
| $I_1$ | 0 | $2\theta$ | 0111, 1011 |
| $I_2$ | 0 | 0 | 0101, 0110, 1001, 1010 |
| $I_3$ | 0 | $-2\theta$ | 0100, 1000 |
| $I_4$ | $2\theta$ | $2\theta$ | 1111 |
| $I_5$ | $2\theta$ | 0 | 1101, 1110 |
| $I_6$ | $2\theta$ | $-2\theta$ | 1100 |
| $I_7$ | $-2\theta$ | $2\theta$ | 0011 |
| $I_8$ | $-2\theta$ | 0 | 0001, 0010 |
| $I_9$ | $-2\theta$ | $-2\theta$ | 0000 |

Eqs. (2) to (4) show that the intensity $I_{out}$ is a function of the parameters: $I_0$, $S_1$, $S_2$, $S_3$, $\theta$, $\theta_{wp}$ and $\Gamma$, and Eq. (1) under different non-degenerate states can be rewritten as:

$$I_j = f(I_0, S_1, S_2, S_3, \theta, \theta_{wp}, \Gamma), j=1, 2, \ldots 9 \quad (4)$$

where $I_j$ is the output power of the WPA for the $i^{th}$ non-degenerate states. Assuming that the Stokes parameters $(S_1, S_2, S_3)$ generated by $P_1$ and QWP (FIG. 1) are known, then input power $I_0$, rotation angle $\theta$, retardance $\Gamma$ and axis orientation $\theta_{wp}$ of the sample can be calculated by numerically solving Eq. (4). Eq. (4) can be solved by numerically searching for the optimized values of $I_0$, $\theta$, $\theta_{wp}$, and $\Gamma$ to minimize $$\sum_j (f_j - I_{j,measured})^2.$$

Notably, the SOP of the input light can be properly selected to achieve high measurement accuracy. For example, when the input light is linearly polarized $(S_3=0)$, the output $I_{out}$ is an even function of the retardance $\Gamma$ of the sample, which means that $-\Gamma$ and $+\Gamma$ will be related to the same output $I_{out}$, thus the WPA cannot identify the slow and fast axis under this condition; moreover, as $S_3=0$, Eq. (2) is reduced to $$I_{out} = \frac{I_0}{2}\{1 + [-(\cos2(\alpha-\theta_{wp})\cos2(\beta+\theta_{wp}) + \sin2(\alpha-\theta_{wp})\sin2(\beta+\theta_{wp})\cos(\Gamma)]S_1 + [\sin2(\alpha-\theta_{wp})\cos2(\beta+\theta_{wp}) + \cos2(\alpha-\theta_{wp})\sin2(\beta+\theta_{wp})\cos(\Gamma)]S_2\}, \quad (5)$$

For the retardance $\Gamma$ is closed to $\pi$, the $I_{out}$ will be insensitive to the change of $\Gamma$, thus the measurement uncertainty will be dramatically increased.

Similarly, when input light is circularly polarized $(S_1=S_2=0, S_3=1)$, the Eq. (1) becomes $$I_{out} = \frac{I_0}{2}[1 + \sin2(\beta+\theta_{wp})\sin\Gamma S_3] \quad (6)$$

Therefore, $I_{out}$ is insensitive to the change of $\Gamma$ when $\Gamma$ is $\sim\pi/2$. In our experiments, we set the SOP of the input light to be $\sim(0.5, 0.5, 0.707)$ by aligning $P_1$ and QWP with a relative angle of 22.5° to each other. Such input SOP control guarantees good retrace measurement accuracy in the range of $(-\pi, \pi)$. It should be noted the retardance of the QWP is generally wavelength and temperature dependent, i.e the SOP of input light is also wavelength and temperature dependent, so it is necessary to calibrate the SOP of the input light during high accuracy measurement. Fortunately, we can get SOP by simply measuring the $I_{out}$ under different status of MO rotators without sample under test. When no sample is inserted, the Eq. (1) can be rewritten as $$I_{out} = \frac{I_0}{2}\{1 + [-(\cos2\alpha\cos2\beta + \sin2\alpha\sin2\beta]S_1 + [\sin2\alpha\cos2\beta + \cos2\alpha\sin2\beta]S_2\} \quad (7)$$

Because the light is totally polarized, the following equation can be obtained.

$$S_1^2 + S_2^2 + S_3^2 = 1 \quad (S_3 > 0) \quad (8)$$

Therefore, after measuring the output powers under different non-degenerated states of MO rotators, the SOP $(S_1, S_2, S_3)$ can be calculated by solving the equations (7) and (8) using the least-square-fitting algorithm.

Figure 2:
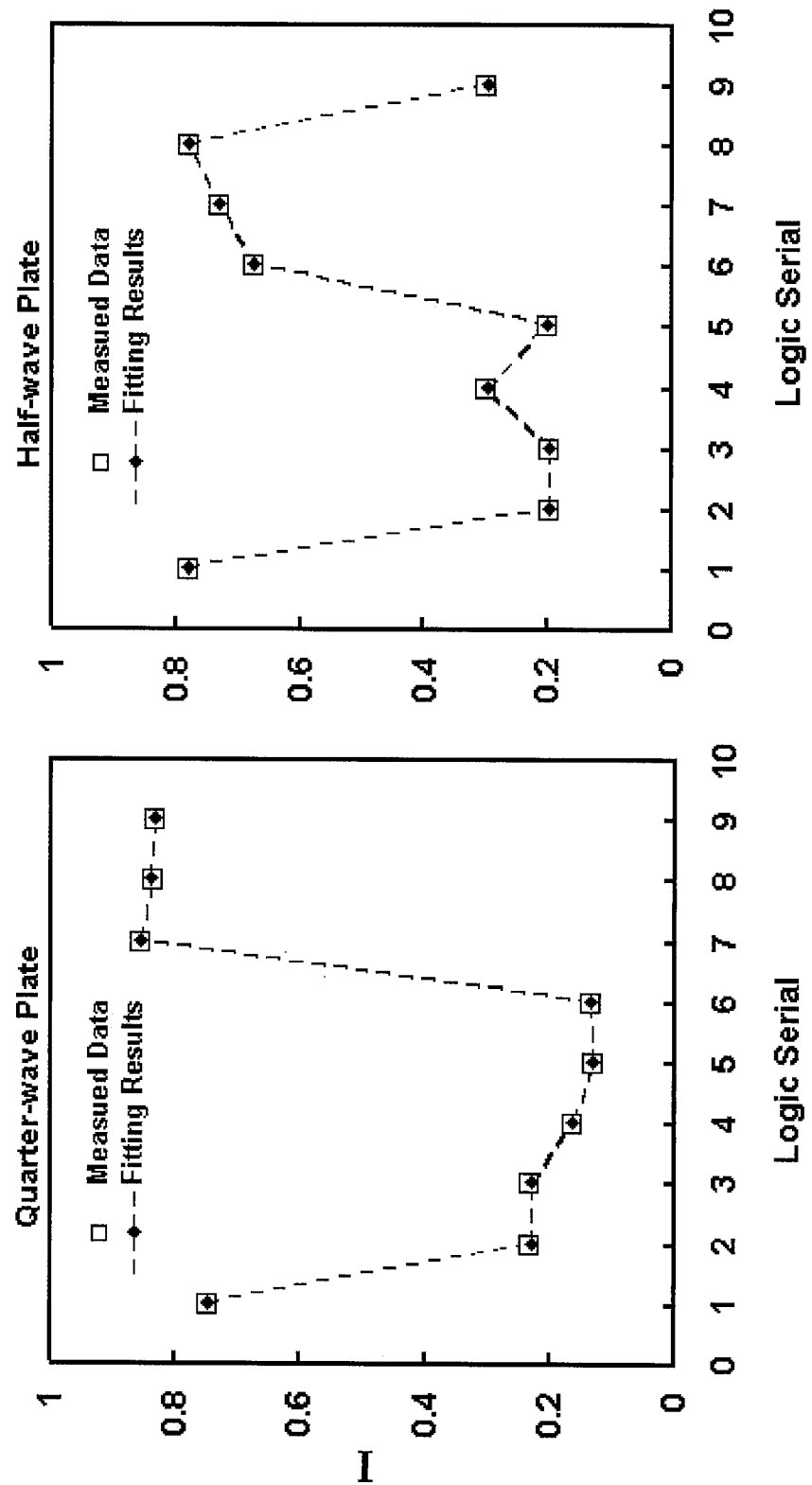
FIG. 2 shows example measurement results with the normalized intensity for the half- and quarter-wave plate based on the WPA device in FIG. 1.

We measured the retardance and the axis orientation of a waveplate sample using following procedure: (i) The SOP of the input light is measured by measuring the $I_{out}$ under 9 non-degenerate logic states without putting in the waveplate sample (Eq. 7 and 8). (ii) $I_{out}$ under 9 non-degenerate logic states are measured after the waveplate sample is inserted; and (iii) the least-square-fitting algorithm is used to calculate the retardance and orientation angle of the sample according to SOP obtained in the first step. The typical measured and fitted data are shown in FIG. 2. All measurements are taken at 1550 nm and the photodetector outputs have been normalized using the input optical power. The nonlinear least-square-fitting results are shown in table 2. The error factor $\sigma$ between the measured and fitted data is calculated as $$\sigma = \sqrt{\frac{(I_{i,Exp} - I_{i,Fitting})^2 / I_0^2}{9}} \quad (9)$$

TABLE 2

Least-square-fitting results for different wave plates

| | Half-Wave Plate | Quarter-Wave Plate | Air (no waveplate) |
|---|---|---|---|
| SOP of the input light | $S_1 = 0.494$, $S_2 = 0.514$, $S_3 = 0.701$ | | |
| Least-square-fitting results | | | |
| Retardation of waveplate $\Gamma$ | 179.68 | 90.41° | 0.057° |
| Orientation angle of waveplate $\theta_{wp}$ | −2.24° | 89.51° | 15.12° |

TABLE 2-continued

Least-square-fitting results for different wave plates

| SOP of the input light | Half-Wave Plate $S_1 = 0.494$ | Quarter-Wave Plate $S_2 = 0.514$ | Air (no waveplate) $S_3 = 0.701$ |
|---|---|---|---|
| Rotation angle of rotators θ | 21.77° | 21.75° | 21.74° |
| Fitting error σ | 0.0016 | 0.0015 | 0.0008 |

The fitting error σ is as low as 0.0016, which shows that Eq. (1) can accurately describe the current WPA system. The measured retardance of 90.4° and 179.64° of the commercial quarter-wave and half-waveplates are consistent with the datasheet from the vendors (90°±/−0.7°, and 180°±/−0.7°, respectively). In order to further check the accuracy of our WPA, we also measure the retardance of the air (Table 2), i.e. without any waveplate sample, the retardance is as low as 0.057°, close to zero. In addition, one hundred measurements are taken to evaluate the repeatability and stability of our WPA system. The standard deviations of the measured retardance are 0.024° and 0.014° for the half-wave and quarter-wave plate, respectively, with 0.070° and 0.014° for the orientation angles of the optical axes.

Figure 3:
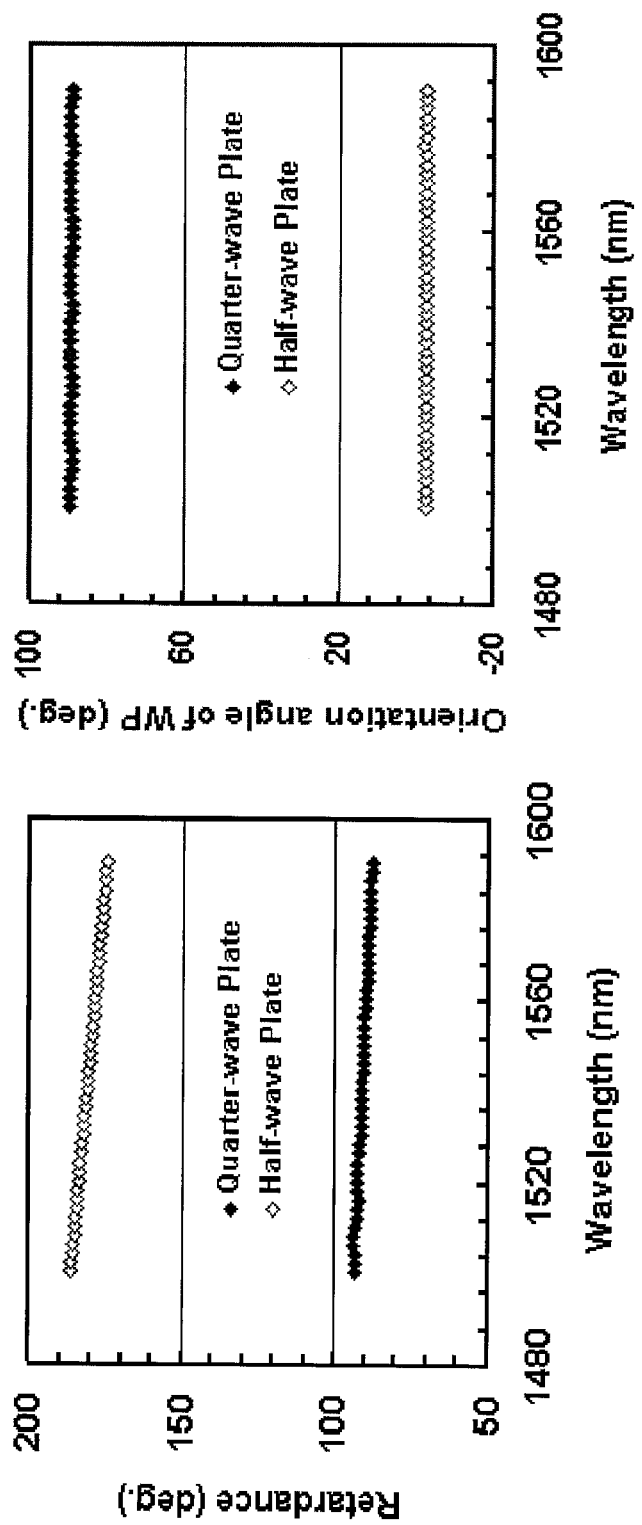
FIG. 3 shows example wavelength dependence curves of the retardance and orientation angle of waveplates measured by the WPA device in FIG. 1.

Using a tunable laser, the MO-based WPA can be used to acquire the wavelength dependence of both the retardance and orientation angle of a waveplate. The typical measured curves are shown in FIG. 3. The slopes of the retardance are abut 0.129°/nm and 0.064°/nm for a zero-order quartz half-wave plate and quarter-wave plate, respectively, which are consistent with the values of 0.135°/nm and 0.068°/nm calculated from the dispersion equations of the quartz crystal. The standard deviations of orientation angles are 0.12° and 0.045° for the half-wave and quarter-wave plate in the wavelength range of 1500 nm-1590 nm, respectively.

Moreover, for the multi-order waveplate, the WPA produces the retardance (0~2π) at a given wavelength. The order of waveplate cannot be calculated only from one wavelength measurement. Generally, the retardance of the waveplate is wavelength dependent, and its slope is related to the order and index of waveplate. A typical test curves of retardance vs. wavelength of multi-order waveplate is shown in the following figures.

Various methods can be used to determine the order of the waveplate. Three examples are described below.

Method 1:

If the approximated thickness L and birefringence $\Delta n(\lambda_0)$ at given wavelength $\lambda_0$ are known, then the order m is:

$$m = \frac{\Delta n(\lambda_0)L}{\lambda_0} - \Gamma(\lambda_0)/360° \quad (9)$$

where $\Gamma(\lambda_0)$ is the retardance measured by WPA at wavelength $\lambda_0$. For example, a waveplate sample has L=1945 μm, $\lambda_0$=1.550 μm, $\Delta n_0$(1.550 μm)=0.008353 and $\Gamma(\lambda_0)$=175.4°, then $$m = \frac{0.008353 * 1945}{1.55} - 175.4°/360° = 9.996 \quad (10)$$

Method 2:

Assuming that the chromatic dispersion near $\lambda_0$ can be ignored, the real retardance Φ of waveplate can be written as $$\Phi = \frac{\Delta n(\lambda)L}{\lambda} * 360 = m*360° + \Gamma(\lambda) \quad (11)$$

where $\Gamma(\lambda)$ is the retardance measured by WPA at wavelength λ. IF $\Delta n(\lambda) \approx \Delta n(\lambda_0)$, then $$\Phi = \frac{\Delta n(\lambda_0)L}{\lambda} * 360 = \frac{\lambda_0 \Delta n(\lambda_0)L}{\lambda \lambda_0} * 360 = \frac{\lambda_0}{\lambda}(m*360° + \Gamma(\lambda_0)) \text{ and} \quad (12)$$

$$\frac{d\Phi}{d(v)} = \lambda_0 * (m*360 + \Gamma(\lambda_0)) \quad (13)$$

where v=1/λ. For example, again, for the same waveplate sample, $$m = \left(\frac{\frac{d\Phi}{d(v)}\big|_{v=v0}}{\lambda_0} - \Gamma_0\right)\bigg/360 = \left(\frac{6501}{1.55} - 175.4\right)\bigg/360 = 11.16 \quad (14)$$

Hence, the order of the waveplate is m=11.16. Here we improve the accuracy by considering the chromatic dispersion of the waveplate sample.

Method 3:

If the $\Delta n(\lambda)$ is known, it is possible to get the proper order of the waveplate sample from the curves of retardance vs. wavelength without measuring the thickness of waveplate. The (12) can be written as $$\Phi = \frac{\Delta n(\lambda)L}{\lambda} \frac{\Delta n(\lambda_0)}{\Delta n(\lambda_0)} \frac{\lambda_0}{\lambda_0} * 360 = \frac{\Delta n(\lambda)\lambda_0}{\Delta n(\lambda_0)\lambda} \frac{\Delta n(\lambda_0)L}{\lambda_0} * 360° = \frac{\lambda_0 \Delta n(\lambda)}{\Delta n(\lambda_0)\lambda} \Phi_0 \quad (15)$$

so $$\frac{d\Phi}{d(v)}\bigg|_{\lambda=\lambda_0} = \frac{\lambda_0}{\Delta n(\lambda_0)}\Phi_0\left(-\frac{\Delta n(\lambda)}{\lambda^2} + \frac{\Delta n'(\lambda)}{\lambda}\right)\bigg|_{\lambda=\lambda_0} \quad (16)$$

$$= \frac{\Phi_0}{\Delta n(\lambda_0)}\left(-\frac{\Delta n(\lambda_0)}{\lambda_0} + \Delta n'(\lambda_0)\right)$$

$$= \Phi_0\left(\frac{\Delta n'(\lambda_0)}{\Delta n(\lambda_0)} - \frac{1}{\lambda_0}\right)$$

and $$\frac{d\Phi}{d(v)}\bigg|_{\lambda=\lambda_0} = \frac{\Phi_0}{\Delta n(v_0)v_0}(\Delta n(v) + v\Delta n'(v))\bigg|_{v=v_0} \quad (17)$$

$$= \frac{\Phi_0}{\Delta n(v_0)}\left(\frac{\Delta n(v_0)}{v_0} + \Delta n'(v)\right)\bigg|_{v=v_0}$$

$$= \Phi_0\left(\frac{1}{v_0} + \frac{\Delta n'(v_0)}{\Delta n(v_0)}\right)$$

$$= \Phi_0\left(\frac{1}{v_0} - \frac{\Delta n'(\lambda_0)}{\Delta n(v_0)v_0^2}\right) = \lambda_0\Phi_0 - \Phi_0\frac{\Delta n'(\lambda_0)}{\Delta n(\lambda_0)}\lambda_0^2$$

where $v = 1/\lambda$ and $\Phi_0 = m*360 + \Gamma_0$, and $\Delta n'(\lambda) = -\Delta n(v)v^2$, so $$m = \left(\frac{\frac{d\Phi}{d(v)}\big|_{v=v_0}}{\lambda_0 - \frac{\Delta n'(\lambda_0)}{n(\lambda_0)}\lambda_0^2} - \Gamma_0\right)\bigg/360° = \left(\frac{\frac{d\Phi}{d(v)}\big|_{\lambda=\lambda_0}}{\frac{1}{\lambda_0} - \frac{\Delta n'(\lambda_0)}{n(\lambda_0)}} - \Gamma_0\right)\bigg/360°. \quad (18)$$

It can be difficult to obtain accurate Δn'(λ) from the dispersion equation of the waveplate. The parameter Δn'(λ) can be accurately measured when the order of waveplate is known. In this method, Eq. (9) is first used to calculate the order m of multi-order waveplate, then the value of Δn'(λ) can be computed from Eq. (18).

Figure 4:
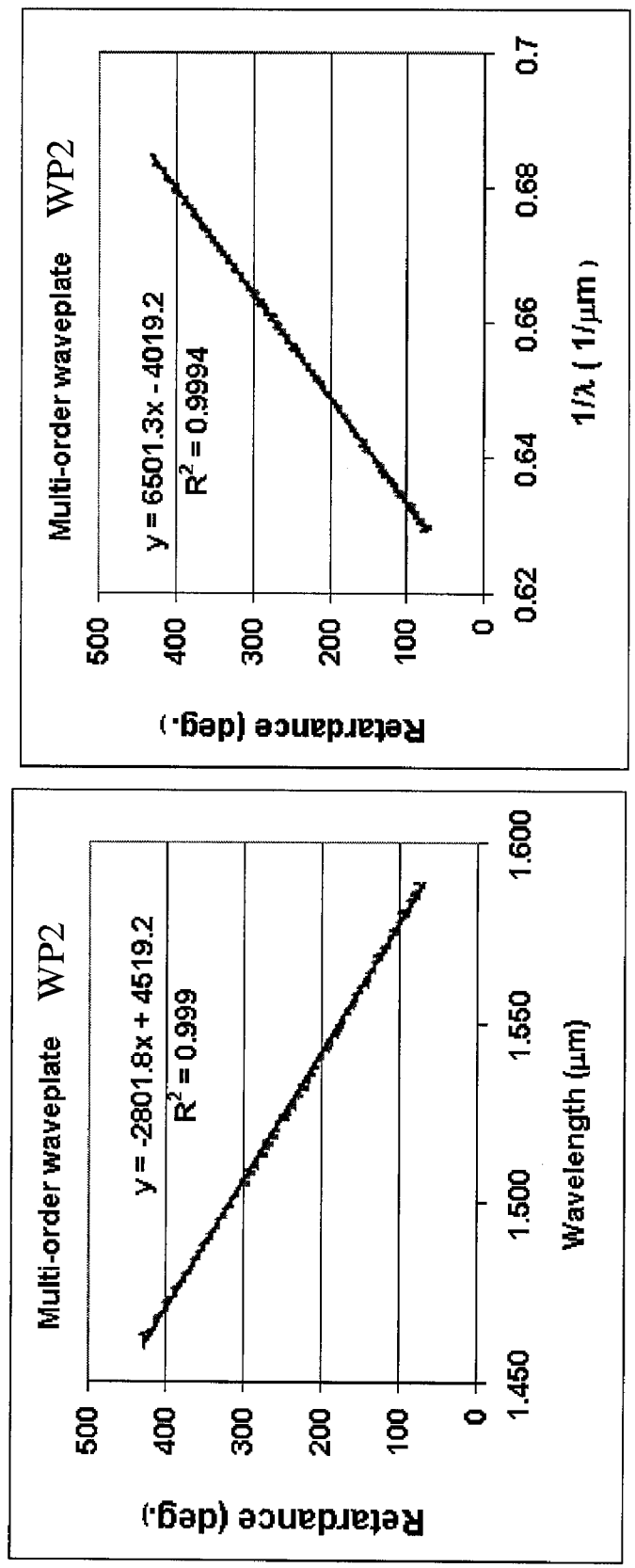
FIG. 4 shows the wavelength dependence of the retardance of a multi-order waveplate.

For example, the waveplate sample in Method 1 and 2 is made from quartz crystal and its thickness L=1945 μm, $\lambda_0$=1.550 μm, $\Delta n_0$ (1.550 μm)=0.008353, $$\Gamma(\lambda_0 = 1550 \text{ nm}) 175.4°, \text{ and}$$

$$\left.\frac{d\Phi}{dv}\right|_{v=v_0} = 6501°/\mu m \text{ (see FIG. 4), then}$$

$$m = \frac{0.008353 * 1945}{1.55} - 175.4°/360° = 9.996 \text{ and}$$

$$\frac{\Delta n'(\lambda_0)}{\Delta n(\lambda_0)} = -\left(\frac{\left.\frac{d\Phi}{dv}\right|_{v=v_0}}{m*360 + \Gamma_0} - \lambda_0\right) \Big/ \lambda_0^2 = -7.157 * 10^{-2} \quad (19)$$

The comparison of the above three methods is listed in Table 3.

TABLE 3

Comparison of three methods for measuring multi-order waveplate

| $\lambda$ = 1550 nm | Thickness (μm) | Retardance | $d\Phi/dv$ (°/μm) ($v_0$ = 1/1.55 μm) | Order of waveplate | | |
|---|---|---|---|---|---|---|
| | | | | Method 1 | Method 2 | Method3 |
| Waveplate 0 | 45 | 90.3 | 152.67 | −0.008 | 0.022 | −0.004 |
| Waveplate 1 | 1953 | 173.5 | 6520 | 10.000 | 11.20 | 10.04 |
| Waveplate 2 | 1945 | 175.4 | 6501 | 9.996 | 11.16 | 10.00 |

While this specification contains many specifics, these should not be construed as limitations on the scope of an invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

Only a few implementations and examples are described, variations and enhancements of the described implementations and examples, and other implementations are possible based on what is described.

What is claimed is:

1. A method for measuring optical birefringence of a sample, comprising:

directing an optical probe beam of an input state of polarization to sequentially pass through (1) at least two adjustable input polarization rotators, (2) a sample under measurement, (3) at least two adjustable output polarization rotators and (4) an output optical polarizer;

directing the optical probe beam to pass through an input optical polarization generator first before directing the optical probe beam into the at least two adjustable input polarization rotators;

using the input optical polarization generator to control the optical probe beam to be at the input state of polarization, wherein the input optical polarization generator includes an input optical polarizer to receive the optical probe beam and a quarter wave plate to receive the optical probe beam from the input optical polarizer;

adjusting the at least two adjustable input polarization rotators and at least two adjustable output polarization rotators to produce a plurality of different states of polarization in the optical probe beam when entering the output optical polarizer;

measuring optical power levels of optical transmission of the optical probe beam through the output optical polarizer at the plurality of different states of polarization of the optical probe beam when entering the output optical polarizer; and performing a numerical processing based on
the input state of polarization of the optical probe beam and
the measured optical power levels at the plurality of different states of polarization on the optical probe beam when entering the output optical polarizer
to determine an amount of the optical retardation of the sample and an orientation of a principal polarization axis of the sample.

2. The method as in claim 1, wherein the numerical processing comprises:

performing a numerical computation based on a Muller matrix formulation and the measured optical power levels, without known values for Muller matrix elements of an optical assembly, which comprises the at least two adjustable input polarization rotators, the sample, the at least two adjustable output polarization rotators and the output optical polarizer, to obtain the amount of the optical retardation of the sample and the orientation of a principal polarization axis of the sample.

3. The method as in claim 2, wherein the numerical computation comprises:

for each collection of rotator settings for the at least two adjustable input polarization rotators and the at least two adjustable output polarization rotators corresponding to a respective state of polarization among the plurality of different states of polarization in the optical probe beam when entering the output optical polarizer, applying presumed values for Stokes parameters of component parameters for the at least two adjustable input polarization rotators and the at least two adjustable output polarization rotators, the sample and the output optical polarizer in the Mueller matrix formulation to compute a power level of the light output from the output optical polarizer;

obtaining a sum of squared values of differences between computed power levels of the light output from the output optical polarizer and respective measured power levels of the light output from the output optical polarizer for the plurality of different states of polarization of the optical probe beam when entering the output optical polarizer;

adjusting at least one of the presumed values for Stokes parameters of the component parameters to search for a selected set of values for the Stokes parameters of the component parameters that minimize the sum; and using values for Stokes parameters in the selected set of values for the sample to obtain the amount of the optical retardation of the sample and the orientation of a principal polarization axis of the sample.

4. The method as in claim 1, comprising:

prior to directing the optical probe beam to sequentially pass through (1) the at least two adjustable input polarization rotators, (2) the sample, (3) the at least two adjustable output polarization rotators and (4) the output optical polarizer, directing the optical probe beam to sequentially pass through (1) the at least two adjustable input polarization rotators, (2) the at least two adjustable output polarization rotators and (3) the output optical polarizer, without the sample;

adjusting the at least two adjustable input polarization rotators and at least two adjustable output polarization rotators to produce a plurality of different states of polarization in the optical probe beam when entering the output optical polarizer without the sample;

measuring optical power levels of optical transmission of the optical probe beam through the output optical polarizer at the plurality of different states of polarization of the optical probe beam when entering the output optical polarizer without the sample; and performing a first numerical processing based on the measured optical power levels at the plurality of different states of polarization on the optical probe beam when entering the output optical polarizer without the sample to determine the input state of polarization of the optical probe beam.

5. The method as in claim 4, wherein the first numerical computation comprises:

for each collection of rotator settings for the at least two adjustable input polarization rotators and the at least two adjustable output polarization rotators corresponding to a respective state of polarization among the plurality of different states of polarization in the optical probe beam when entering the output optical polarizer without the sample, applying presumed values for, Stokes parameters of the input state of polarization of the optical probe beam, and component parameters for the at least two adjustable input polarization rotators and the at least two adjustable output polarization rotators, and the output optical polarizer in the Mueller matrix formulation, to compute a power level of the light output from the output optical polarizer;

obtaining a sum of squared values of differences between computed power levels of the light output from the output optical polarizer and respective measured power levels of the light output from the output optical polarizer for the plurality of different states of polarization of the optical probe beam when entering the output optical polarizer without the sample;

adjusting at least one of the presumed values for Stokes parameters of the component parameters to search for a selected set of values for the Stokes parameters of the input state of polarization of the optical probe beam and the component parameters that minimize the sum; and using values for Stokes parameters in the selected set of values for the input state of polarization of the optical probe beam as the actual input state of polarization of the optical probe beam in subsequent processing for determining the amount of the optical retardation of the sample and the orientation of a principal polarization axis of the sample.

6. The method as in claim 1, wherein each adjustable polarization rotator has two different polarization rotation angles and operates as a binary device to rotate polarization of light at either of the two different polarization rotation angles.

7. The method as in claim 6, wherein the two different polarization rotation angles for each adjustable polarization rotator are set to be at +22.5 degrees and 22.5 degrees.

8. The method as in claim 6, wherein each adjustable polarization rotator is a magneto-optic rotator.

9. The method as in claim 1, wherein the numerical processing further comprises:

calibrating a change in a parameter in each of (1) the at least two adjustable input polarization rotators, (2) the at least two adjustable output polarization rotators and (3) the output optical polarizer caused by a change in temperature or in an optical wavelength of light.

10. The method as in claim 1, further comprising:

adjusting an optical wavelength of the optical probe beam to be at different optical probe wavelengths; and at each different optical probe wavelength, determining a respective amount of the optical retardation of the sample and a respective orientation of the principal polarization axis of the sample.

11. A device for measuring optical birefringence of a sample, comprising:

an input optical polarization element operable to receive an optical probe beam and to output the optical probe beam at an input state of polarization, wherein the input optical polarization element comprises an input optical polarizer to receive the optical probe beam, and a quarter wave plate to receive the optical probe beam from the input optical polarizer wave plate;

at least two adjustable input polarization rotators positioned to receive the optical probe beam from the input optical polarization element and each operable to rotate polarization of light;

a sample holder operable to hold a sample and positioned to placed the sample in an optical path of the optical probe beam downstream from the at least two adjustable input polarization rotators;

at least two adjustable output polarization rotators positioned downstream from the sample holder to receive the optical probe beam that passes through the sample holder and each operable to rotate polarization of light;

an output optical polarizer positioned to receive the optical probe beam from the at least two adjustable output polarization rotators to produce an output optical probe beam polarized in a direction along a polarization direction of the output optical polarizer;

a photodetector positioned to receive the output optical probe beam from the output optical polarizer and operable to measure a power level of the output optical probe beam; and a control and processing unit operable to control the adjustable input and output polarization rotators to be at different collections of rotator settings to generate different states of polarization in the optical probe beam after transmitting through the at least two adjustable output polarization rotators to obtain different power levels of the output optical probe beam at the photodetector, respectively, wherein the control and processing unit is programmed to perform a numerical processing based on the input state of polarization of the optical probe beam when exiting the input optical polarization element and the measured optical power levels at the plurality of different states of polarization of the optical probe beam when entering the output optical polarizer to determine an amount of the optical retardation of the sample and an orientation of a principal polarization axis of the sample.

12. The device as in claim 11, wherein each adjustable polarization rotator is a magneto-optic (MO) rotator.

13. The device as in claim 12, wherein each adjustable polarization rotator is responsive to a first control signal to rotate polarization by a fixed angle in a first direction, and responsive to a second control signal to rotate the polarization by the fixed angle in a second, opposite direction.

14. The device as in claim 11, further comprising:
a tunable laser operable to produce the optical probe beam and to adjust an optical wavelength of the optical probe beam in response to a control from the control and processing unit.

* * * * *

UNITED STATES PATENT AND TRADEMARK OFFICE
CERTIFICATE OF CORRECTION

| | | |
|---|---|---|
| PATENT NO. | : 7,952,711 B1 | Page 1 of 1 |
| APPLICATION NO. | : 12/056262 | |
| DATED | : May 31, 2011 | |
| INVENTOR(S) | : Xiaojun Chen, Lianshan Yan and Xiaotian Steve Yao | |

It is certified that error appears in the above-identified patent and that said Letters Patent is hereby corrected as shown below:

In Column 4, Line 63, in Equation 2, delete "$\beta = \sum_{n=3}^{4} -(-1)^{bn}\theta.$" and insert -- $\beta = \sum_{n=3}^{4} -(-1)^{bn}\theta$ --, therefor.

In Column 5, Line 62, in Equation 5, delete "$\cos 2(\alpha - \theta_{wp})\sin 2(\beta + \theta_{wp})\cos(\Gamma)]S_2\},$" and insert -- $\cos 2(\alpha - \theta_{wp})\sin 2(\beta + \theta_{wp})\cos(\Gamma)]S_2]$. --, therefor.

In Column 7, Line 15, delete "(90°±/-0.7°, and 180°±/-0.7°," and insert -- (90°±0.7°, and 180°±0.7°, --, therefor.

In Column 7, Line 35, delete "1500 nm-1590 nm," and insert -- 1500 nm~1590 nm --, therefor.

In Column 8, Lines 36-37, in Equation 16, delete "$\frac{d\Phi}{d(v)}\big|_{\lambda=\lambda_0}$" and insert -- $\frac{d\Phi}{d\lambda}\big|_{\lambda=\lambda_0}$ --, therefor.

In Column 8, Line 55, delete "-Δn(v)v²," and insert -- -Δn'(v)v², --, therefor.

In Column 10, Line 36, in Claim 2, delete "Muller" and insert -- Mueller --, therefor.

In Column 10, Line 38, in Claim 2, delete "Muller" and insert -- Mueller --, therefor.

Signed and Sealed this
Twentieth Day of March, 2012

David J. Kappos
*Director of the United States Patent and Trademark Office*